US012564576B2

(12) United States Patent
Era et al.

(10) Patent No.: US 12,564,576 B2
(45) Date of Patent: Mar. 3, 2026

(54) THERAPEUTIC AGENT FOR VASCULAR DISORDER

(71) Applicant: NATIONAL UNIVERSITY CORPORATION KUMAMOTO UNIVERSITY, Kumamoto (JP)

(72) Inventors: Takumi Era, Kumamoto (JP); Sayaka Watanabe, Tokyo (JP); Tomoe Kusayanagi, Tokyo (JP)

(73) Assignee: National University Corporation Kumamoto University, Kumamoto (JP)

( * ) Notice: Subject to any disclaimer, the term of this patent is extended or adjusted under 35 U.S.C. 154(b) by 707 days.

(21) Appl. No.: 17/998,195

(22) PCT Filed: May 7, 2021

(86) PCT No.: PCT/JP2021/017423
§ 371 (c)(1),
(2) Date: Nov. 8, 2022

(87) PCT Pub. No.: WO2021/225149
PCT Pub. Date: Nov. 11, 2021

(65) Prior Publication Data
US 2023/0210828 A1     Jul. 6, 2023

(30) Foreign Application Priority Data
May 8, 2020     (JP) ................................. 2020-082511

(51) Int. Cl.
*A61K 31/436*     (2006.01)
*A61P 9/14*     (2006.01)

(52) U.S. Cl.
CPC .............. *A61K 31/436* (2013.01); *A61P 9/14* (2018.01)

(58) Field of Classification Search
CPC .... A61P 11/00; A61P 9/00; A61P 9/12; A61P 9/14; A61K 31/43
See application file for complete search history.

(56) References Cited

U.S. PATENT DOCUMENTS

| | | | |
|---|---|---|---|
| 2010/0166869 A1 | 7/2010 | Desai et al. | |
| 2013/0317053 A1 | 11/2013 | Kaneda et al. | |
| 2014/0037548 A1 | 2/2014 | Rosen et al. | |

FOREIGN PATENT DOCUMENTS

| | | |
|---|---|---|
| CN | 102499919 | 6/2012 |
| WO | 2012/105521 | 8/2012 |

OTHER PUBLICATIONS

Feng, et al., "Protective Effect of Rapamycin on Kidney in Diabetic Rats", Tianjin Med J, Jun. 2011, vol. 39, No. 6, pp. 548-551, including English abstract.

(Continued)

*Primary Examiner* — Savitha M Rao
(74) *Attorney, Agent, or Firm* — HSML P.C.

(57) ABSTRACT

An object is to provide a drug that effectively treats a vascular disorder caused by excessive synthesis and secretion of a type IV collagen protein from a vascular endothelial cell. Provided are [1] a therapeutic agent for a vascular disorder associated with excessive synthesis and secretion of a type IV collagen protein; [2] a therapeutic agent for a disease caused by excessive synthesis and secretion of a type IV collagen protein; [3] a pharmaceutical composition for treatment of a vascular disorder associated with excessive synthesis and secretion of a type IV collagen protein; [4] a pharmaceutical composition for treatment of a disease caused by excessive synthesis and secretion of a type IV collagen protein from a vascular endothelial cell; and [5] an agent that inhibits excessive synthesis and secretion of a type IV collagen protein from a vascular endothelial cell, (Continued)

TYPE IV COLLAGEN PROTEIN each of [1] to [5] containing sirolimus as an active ingredient.

6 Claims, 1 Drawing Sheet

(56)                    References Cited

OTHER PUBLICATIONS

Fried, et al., "Efficacy of Rapamycin in Scleroderma: A Case Study", Lymphat Res Biol. 2008; 6(3-4): 217-219.
Luo, et al., "AMP-Activated Protein Kinase Alleviates Extracellular Matrix Accumulation in High Glucose-Induced Renal Fibroblasts through mTOR Signaling Pathway", Cell Physiol Biochem 2015;35:191-200.
Juhl, et al., "Type III, IV, and VI Collagens Turnover in Systemic Sclerosis—a Longitudinal Study", Scientific Reports (2020) 10:7145, 6 pages.
First Office Action issued in corresponding Chinese Patent Application No. 202180027906.0, Oct. 11, 2023, 8 pages with machine translation.
International Search Report issued in International Application No. PCT/JP2021/017423, Jul. 13, 2021, 2 pages.
Written Opinion issued in International Application No. PCT/JP2021/017423, Jul. 13, 2021, 5 pages.
Gabrielli, et al., "Mechanisms of Disease Scleroderma", The New England Journal of Medicine, 360:19, May 7, 2009, 1989-2003.
"Abstracts Poster", American Journal of Transplantation, Blackwell Munksgaard, DK, vol. 8, Apr. 10, 2009, pp. 384-729.
Rangan, "Therapeutic role of sirolimus in non-transplant kidney disease", Pharmacology & Therapeutics, 123:2, Aug. 1, 2009 187-206.
Gendy, et al., "Selective inhibition of cyclooxygenase-2 suppresses metastatic disease without affecting primary tumor growth in a murine model of Ewing sarcoma", Journal of Pediatric Surgery 46:1, Jan. 1, 2011, 108-114.
Liang, et al., "Effects of high glucose and Rapamycin intervention on expression of type IV collagen and matrix metalloproteinase-9 in podocytes", Journal of Shanghai Jiaotong University (Medical Science), 30:5, May 2010, 518-522, English Abstract.
Lock, et al., "Rapamycin at subimmunosuppressive levels inhibits mesangial cell proliferation and extracellular matrix production", Lock, et al., Am J Physiol Renal Physiol 292:1, F76-F81, Jan. 2007.
Zhang, et al., "The Small Leucine-Rich Proteoglycan BGN Accumulates in CADASIL and Binds to NOTCH3", Transl. Stroke Res. (2015) 6:148-155.
Yang, et al., "A Novel Rabbit Model for Benign Biliary Stricture Formation and the Effects of Medication Infusions on Stricture Formation", Digestive Diseases and Sciences (2018) 63:10 2653-2661.
Extended European Search Report issued in corresponding European Patent Application No. 21799741.0, Apr. 23, 2024, 13 pages.

TYPE IV COLLAGEN PROTEIN

THERAPEUTIC AGENT FOR VASCULAR DISORDER

TECHNICAL FIELD

The present invention relates to a therapeutic agent for a vascular disorder containing sirolimus as an active ingredient.

BACKGROUND ART

Vascular disorders may cause a variety of serious symptoms. In particular, vascular disorders in peripheral blood vessels exhibit Raynaud's phenomenon, necrosis, and the like, which significantly deteriorate patients' QOL, and may lead to death when serious symptoms occur not only in the periphery but also in each tissue. Therefore, treatment of systemic vascular disorders is very important.

Conventionally, it has been considered that many of peripheral vascular disorders or blood flow disorders including Raynaud's phenomenon are caused by loss of capillaries due to abnormal accumulation of an extracellular matrix, functional deterioration due to hypoxia, and the like. There are various hypotheses as to the cause of this, but the direct cause is unknown. Some reasons such as environmental factors, external stimuli, or immune abnormalities in the body are considered to trigger abnormalities in vascular endothelial cells and vascular smooth muscle cells, and it is considered that accumulation of collagen proteins among excessively produced extracellular matrices contributes to thickening of a blood vessel wall (for example, Non Patent Literature 1).

Until now, for the treatment of vascular disorders, symptomatic treatment including administration of a drug having a vasodilating action has been performed, and treatment such as fundamentally removing the cause of the disease (radical therapy) has not been performed. At least, there is no drug that acts directly on extracellular matrix accumulation in blood vessels.

Peripheral vascular disorders including Raynaud's phenomenon may occur with scleroderma, but scleroderma treatment guidelines (Clinical Practice Guidelines for Systemic Scleroderma by the Japanese Dermatological Association) describe a therapy with *digitalis* preparations containing digoxin as a basic therapy for pulmonary hypertension associated with scleroderma.

CITATION LIST

Non Patent Literature

Non Patent Literature 1: Armando Gabrielli, et al., N Engl J Med. 2009; 360(19):1989-2003

SUMMARY OF INVENTION

Technical Problem

In the treatment of vascular disorders, it can be said that it is preferable to perform treatment such as fundamentally removing the cause of the disease, but no drug capable of such treatment has been disclosed so far. Also, no drug related to peripheral vascular disorders occurring with scleroderma is disclosed. In view of such circumstances, it is an object of the present invention to provide a drug that effectively treats a peripheral vascular disorder caused by abnormal accumulation of an extracellular matrix, particularly excessive synthesis and secretion of a type IV collagen protein.

Solution to Problem

As a result of studies, the present inventors have found for the first time that type IV collagen genes are mainly highly expressed in vascular endothelial cells derived from iPS cells from patients exhibiting vascular disorders. A type IV collagen protein is abundant mainly in a basement membrane adjacent to a vascular endothelial cell, and is synthesized and secreted by the vascular endothelial cell. Then, the present inventors have found that the synthesis and secretion of a type IV collagen protein in a vascular endothelial cell can be effectively inhibited by causing sirolimus to act on the vascular endothelial cell, thereby completing the present invention.

In other words, the present invention is the following [1] to [5].

[1] A therapeutic agent for a vascular disorder associated with excessive synthesis and secretion of a type IV collagen protein, the therapeutic agent containing sirolimus as an active ingredient.

[2] A therapeutic agent for a disease caused by excessive synthesis and secretion of a type IV collagen protein from a vascular endothelial cell, the therapeutic agent containing sirolimus as an active ingredient.

[3] A pharmaceutical composition for treatment of a vascular disorder associated with excessive synthesis and secretion of a type IV collagen protein, the pharmaceutical composition containing sirolimus as an active ingredient and further containing a pharmaceutically acceptable carrier.

[4] A pharmaceutical composition for treatment of a disease caused by excessive synthesis and secretion of a type IV collagen protein from a vascular endothelial cell, the pharmaceutical composition containing sirolimus as an active ingredient and further containing a pharmaceutically acceptable carrier.

[5] An agent that inhibits excessive synthesis and secretion of a type IV collagen protein from a vascular endothelial cell, the agent containing sirolimus as an active ingredient.

Advantageous Effects of Invention

According to the present invention, it is possible to inhibit the synthesis and secretion of a type IV collagen protein in a vascular endothelial cell, and it is possible to effectively treat a vascular disorder such as a peripheral vascular disorder caused by excessive accumulation of an extracellular matrix containing collagen.

DESCRIPTION OF EMBODIMENTS

Figure 1:
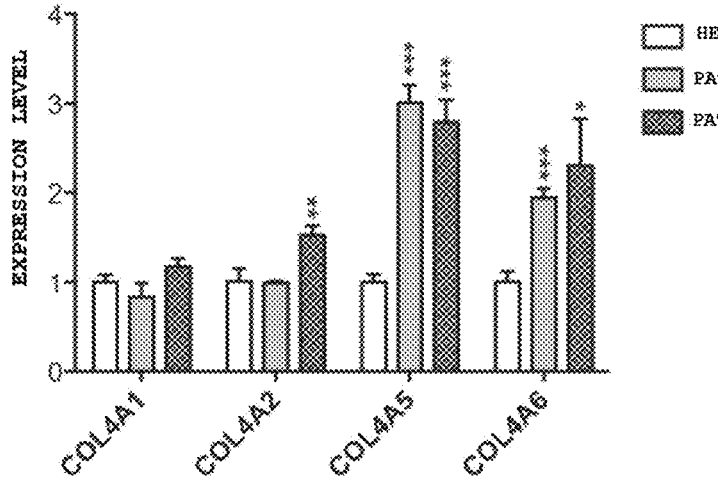
FIG. 1 is a graph showing confirmation results of an expression status of type IV collagen genes in vascular endothelial cells (1 case, 2 cell lines) derived from healthy adults and patients with scleroderma. COL4A1 represents a type IV collagen $\alpha1$ gene, COL4A2 represents a type IV collagen $\alpha2$ gene, COL4A5 represents a type IV collagen $\alpha5$ gene, and COL4A6 represents a type IV collagen $\alpha6$ gene.

The present invention relates to:

[1] a therapeutic agent for a vascular disorder associated with excessive synthesis and secretion of a type IV collagen protein;

[2] a therapeutic agent for a disease caused by excessive synthesis and secretion of a type IV collagen protein;

[3] a pharmaceutical composition for treatment of a vascular disorder associated with excessive synthesis and secretion of a type IV collagen protein;

[4] a pharmaceutical composition for treatment of a disease caused by excessive synthesis and secretion of a type IV collagen protein from a vascular endothelial cell; and

[5] an agent that inhibits excessive synthesis and secretion of a type IV collagen protein from a vascular endothelial cell, each of [1] to [5] containing sirolimus as an active ingredient.

Sirolimus (also known as rapamycin) is a metabolite of the actinomycete *Streptomyces hygroscopicus* isolated from Easter Island soil and was found in the 1970's as a macrolide antibiotic. Thereafter, sirolimus was found to have an immunosuppressive action, and has been approved as a pharmaceutical product that suppresses rejection after kidney transplantation in 55 countries worldwide.

The vascular disorder to be treated with the therapeutic agent for a vascular disorder associated with excessive synthesis and secretion of a type IV collagen protein according to the present invention is typically, but not limited to, a peripheral vascular disorder. For example, vascular disorders and the like caused by overproduction of an extracellular matrix containing collagen, such as vascular disorders that develop due to scleroderma, can be treated with the therapeutic agent according to the present invention. Specific examples thereof include Raynaud's syndrome, which is one of the typical symptoms of scleroderma, pulmonary hypertension, interstitial lung disease, fibrosis of a digestive system, fibrosis of a kidney, fibrosis of a heart, and other vascular lesions associated with Raynaud's syndrome.

In the therapeutic agent for a disease caused by excessive synthesis and secretion of a type IV collagen protein from a vascular endothelial cell, the therapeutic agent containing sirolimus as an active ingredient according to the present invention, the disease is selected from the following (1) to (3):

(1) a peripheral vascular disorder developed due to scleroderma;

(2) Raynaud's syndrome; and (3) the following diseases associated with Raynaud's syndrome: pulmonary hypertension, interstitial lung disease, fibrosis of a digestive system, fibrosis of a kidney, fibrosis of a heart, or other vascular lesions.

The pharmaceutical composition according to the present invention contains a pharmaceutically acceptable carrier in addition to sirolimus as an active ingredient, and can be used in the form of an oral preparation or an external preparation used by being directly applied to an affected area from the outside. In particular, the pharmaceutical composition is preferably used in the form of an oral preparation for a subject to be treated (patient) who has developed a vascular disorder due to a systemic disease. Such a pharmaceutical composition can be produced by a conventionally known method.

The oral preparation according to the present invention can be, for example, a tablet, an orally disintegrating tablet, a capsule, or a granule. The oral preparation contains a pharmaceutically acceptable carrier such as an excipient, an additive, and/or a vehicle that is usually used as long as the effect of sirolimus as an active ingredient is not impaired. As such a pharmaceutically acceptable carrier, for example, a carrier selected from a binder, a disintegrant, a lubricant, a plasticizer, a surfactant, a stabilizer, an antioxidant, a coating agent, a sweetener, a colorant, a fragrance and the like can be used.

Specific examples of the usable carriers include anhydrous lactose, lactose hydrate, crystalline cellulose, mannitol, macrogol 400, polyethylene glycol, polyoxyethylene (160) polyoxypropylene (30) glycol, glycerin monooleate, calcium sulfate and the like as binders; dextran, low-substituted hydroxypropyl cellulose, corn starch, partially pregelatinized starch, carmellose sodium, hypromellose and the like as binders; sodium carboxymethyl starch and the like as disintegrants; magnesium stearate, talc, sodium stearyl fumarate, stearic acid, light anhydrous silicic acid, hydrated silicon dioxide and the like as lubricants; triethyl citrate, propylene glycol and the like as plasticizers; glycerin monostearate, sodium lauryl sulfate, polysorbate 80, polysorbate 60 and the like as surfactants; xanthan gum, polyvinylpyrrolidone, urea and the like as stabilizers; butyl parahydroxybenzoate, tocopherol, ascorbic acid and the like as antioxidants; Eudragid, carnauba wax, hypromellose, or derivatives thereof and the like as coating agents; xylitol and the like as sweeteners; titanium oxide and the like as colorants; and menthol and the like as fragrances.

The external preparation according to the present invention can be in a generally used form such as an ointment, a cream, a lotion, or a gel. Such an external preparation can be prepared by dissolving or dispersing sirolimus as an active ingredient in an appropriate solvent, and then blending a pharmaceutically acceptable carrier such as an excipient or additive that is usually used, such as a gelling agent, a thickener, a pH adjuster, or a stabilizer.

Dosage and Administration

The oral preparation that is one embodiment of the therapeutic agent according to the present invention can be used in the same manner as an ordinary oral preparation, for example, by taking the oral preparation together with water. The dose is appropriately determined depending on the type of the target disease, the severity of the disease, or the condition of the subject to be treated (patient). Usually, 1 to 4 mg/day of sirolimus is orally administered to an adult.

The external preparation that is one embodiment of the therapeutic agent according to the present invention can be used in the same manner as an ordinary external preparation used for a skin disease or the like, such as directly applying the external preparation to an affected area. The dose is appropriately determined depending on the type of the target disease, the severity of the disease, or the condition of the subject to be treated (patient). Usually, a dose corresponding to 0.1 to 2 mg/day of sirolimus for an adult can be used by being directly applied to the skin around an affected area.

EXAMPLES

Although the present invention will be described below with reference to specific embodiments, it will be understood that the present invention is not limited to the embodiments, and that various changes and modifications therein may be made by those skilled in the art without departing from the scope or spirit of the present invention as defined in the appended claims.

Examples (1) Culture of Vascular Endothelial Cells Derived from Patient iPS Cells As the cells, iPS cells derived from healthy adults and patients with scleroderma established at Kumamoto University were used (Zhongzhi Wang, et al., JDS 2016 November; 84(2): 186-196.). Scleroderma is known to cause Raynaud's syndrome, which is one of peripheral vascular disorders, as a symptom of scleroderma, and therefore was employed as a vascular disorder model cell.

Differentiation induction into vascular endothelial cells was performed by culturing iPS cells derived from healthy adults and patients with scleroderma under the conditions described in Table 1.

TABLE 1

| Composition of medium for differentiation induction of vascular endothelial cells | | |
| --- | --- | --- |
| Day | Medium | Growth Factor |
| Day0 | StemPro ™ 34 | BMP4(50 μg/ml), bFGF(50 μg/ml) |
| Day1~2 | SFM | VEGF(40 μg/ml), bFGF(50 μg/ml) |
| Day3~4 | | VEGF(40 μg/ml), bFGF(50 μg/ml), SB431532(20 μM) |
| Day5 | | VEGF(40 μg/ml), bFGF(50 μg/ml), SB431532(20 μM) |

As the obtained cells, only cells positive for VE-cadherin (CD144) and PECAM-1 (CD31), which are vascular endothelial cell markers, were sorted using flow cytometry. From the morphology of the sorted cells and the expression of the marker genes, it was confirmed that the sorted cells were vascular endothelial cells.

The sorted vascular endothelial cells derived from iPS cells from healthy adults and patients with scleroderma were cultured in a 10% FBS-containing Humedia EB-2+ Growth Factor medium (hereinafter referred to as serum-containing medium) shown in the lower part of Table 2, and expanded to passage 3. Approximately $1 \times 10^5$ cultured cells were seeded on a 6-well plate (coated with type I collagen) using the medium, and cultured for 1 day in an incubator at 37° C., 5% $CO_2$.

TABLE 2

| Composition of medium for culture of vascular endothelial cells | | |
| --- | --- | --- |
| Medium | Growth Factor | Serum |
| Humedia EB-2 | B27(2%), bFGF(10 μg/ml), VEGF(20 μg/ml) | — |
| | bFGF(25 μg/ml), VEGF(20 μg/ml) | 10% FBS |

After confirming that the cells were fixed to the bottom of the plate, the medium of the supernatant was removed, and the medium in the plate was washed with PBS. The whole was divided into two parts, and for cells for RNA recovery, using the serum-containing medium, a medium containing 0.25% of DMSO as a vehicle control substance or containing 1 μmol/L of sirolimus as test substance 1 and 0.25% of DMSO was prepared. For cells for recovery of proteins in cell supernatant, a Humedia EB-2+ Growth Factor medium without FBS (hereinafter referred to as serum-free medium) shown in the upper part of Table 2 was used to prepare a medium so that the medium was under the same conditions as mentioned above. Each of the prepared media was added to the plate on which the cells were engrafted and cultured in an incubator at 37° C. and 5% $CO_2$ concentration for 3 days.

(2) Confirmation of Type IV Collagen Gene Expression in Vascular Endothelial Cells Among the cultured cells obtained in the above (1), the cells cultured in the serum-containing medium were used to confirm the expression level of type IV collagen genes in vascular endothelial cells derived from iPS cells from healthy adults and patients with scleroderma by the following procedure.

After 3 days of culture, the supernatant (medium) was removed from the plate, and the inside of the plate was washed using PBS. An RNA extraction reagent (product name: Sepasol®-RNA I Super G, manufactured by Nacalai Tesque, Inc.) were added and cells were recovered, and then the cell suspension was transferred to a container. Chloroform was added thereto, and the mixture was stirred and centrifuged at 4° C. and 12,000 rpm for 15 minutes. Thereafter, only the separated chloroform layer was collected in another container, and RNA was purified using an ethanol precipitation method. cDNA was synthesized from the purified RNA using a reverse transcriptase (product name: SuperScript™ III Reverse Transcriptase, manufactured by Invitrogen™), and the expression level of type IV collagen genes was confirmed by a qPCR method using a fluorescent reagent (product name: THUNDERBIRD® SYBR® qPCR Mix, manufactured by Toyobo Co., Ltd.).

The results are shown in FIG. 1. In vascular endothelial cells derived from patients with scleroderma, it was confirmed that type IV collagen genes (in particular, type IV collagen α5 and α6 genes) were more highly expressed compared with vascular endothelial cells derived from healthy adults. As mentioned above, it is known that patients with scleroderma develop Raynaud's syndrome, which is one of peripheral vascular disorders, as one of the typical symptoms of scleroderma. Therefore, this result strongly suggests that high expression of type IV collagen genes is involved in thickening of a blood vessel wall.

(3) Confirmation of Influence of Sirolimus on Synthesis and Secretion of Type IV Collagen Protein in Vascular Endothelial Cells In the above (1), using the cell supernatant cultured in the serum-free medium, the amount of a type IV collagen protein released into the medium was quantified by the following method.

First, proteins released into the medium were concentrated. In this operation, it is necessary to perform culture under serum-free conditions considering the influence of proteins contained in serum. For 3 days, only the cell supernatant of the cells cultured in the serum-free medium was recovered, cooled acetone in an amount 4 times the amount of the recovered medium was added thereto, and the mixture was allowed to stand at −20° C. overnight. On the next day, after centrifugation at 4° C. and 1000 G for 10 minutes, the supernatant was removed, 75% ethanol was added to the precipitate, the mixture was stirred, and centrifugation was performed again under the same conditions. After removal of ethanol, the precipitate was dried and dissolved in an RIPA buffer, and each sample was adjusted to have a protein concentration of 1 mg/ml using a protein quantification reagent (Bradford Protein Assay, manufactured by Bio-Rad Laboratories, Inc.). After the adjustment, the protein was denatured by heat block at 95° C., and Western blotting was performed. Each sample was applied to a gel (SuperSep™ Ace 5 to 12%, manufactured by FUJIFILM Wako Pure Chemical Corporation) and after electrophoresis, it was transferred to a membrane (Immobilon-P membrane, manufactured by Merck & Co., Inc.). A Goat Anti-Type IV Collagen antibody (Southern Biotech) was used as a primary antibody, and an HRP-labeled antibody (manufactured by Bio-Rad Laboratories, Inc.) was used as a secondary antibody. After the antibody reaction, a type IV collagen protein was detected with a lumino image analyzer (ImageQuant LAS 4000mini, manufactured by GE Healthcare Japan Corporation) using an HRP chemiluminescent reagent (Immobilon® Western blotting detection reagent, manufactured by Merck & Co., Inc.).

Figure 2:
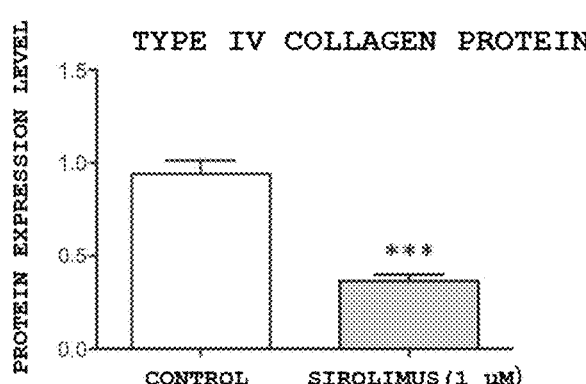
FIG. 2 is a graph showing the difference in the amount of a type IV collagen protein depending on the presence or absence of sirolimus in a medium.

The results are shown in FIG. 2. As shown in this figure, the amount of a type IV collagen protein in the medium containing test substance 1 (sirolimus) was significantly smaller than that in the vehicle control medium. This result indicates that the synthesis and secretion of a type IV collagen protein in a vascular endothelial cell were inhibited by containing sirolimus. As mentioned above, scleroderma causes thickening of a blood vessel wall for some reason. Therefore, in combination with our experimental results shown in the above (2), it was suggested that high expression of type IV collagen genes in a vascular endothelial cell is responsible for this disorder, and sirolimus has an effect of reducing the amount of a type IV collagen protein. Therefore, it was shown that the present drug effectively acts as a therapeutic agent for peripheral vascular disorders caused by overproduction of an extracellular matrix containing collagen such as Raynaud's syndrome.

Comparative Example

The same operation as in Examples was carried out using a medium containing 10 nmol/L of test substance 2 (digoxin) instead of the medium containing test substance 1 in the above (1), and the influence of the presence of digoxin on the expression of type IV collagen was confirmed.

Figure 3:
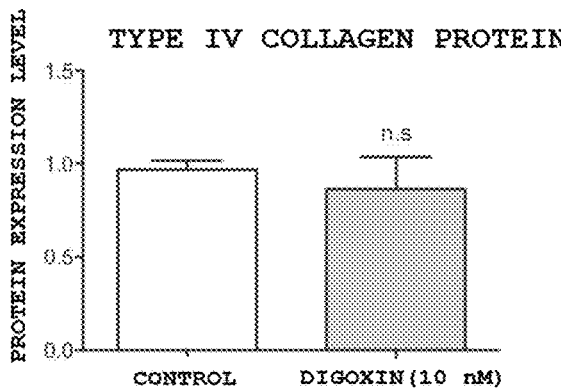
FIG. 3 is a graph showing the difference in the amount of a type IV collagen protein depending on the presence or absence of digoxin in a medium.

The results are shown in FIG. 3. As shown in this figure, the amount of a type IV collagen protein in the medium was hardly reduced in the medium containing digoxin, suggesting that digoxin has a low therapeutic effect on peripheral vascular disorders. *Digitalis* preparations containing digoxin are described in scleroderma treatment guidelines (Clinical Practice Guidelines for Systemic Scleroderma by the Japanese Dermatological Association) as a basic therapy for pulmonary hypertension associated with scleroderma. In addition, the effect of a similar substance of a cardiac glycoside containing digoxin on fibrotic diseases has been reported in a plurality of publications and the like. Contrary to such conventional findings, the results obtained by us show that the effect of digoxin cannot be expected at least for peripheral vascular disorders, and on the other hand, sirolimus whose therapeutic effect is neither described nor suggested in the guidelines exhibits an effect for the treatment of peripheral vascular disorders caused by overproduction of an extracellular matrix containing type IV collagen.

The invention claimed is:

1. A method for treating a peripheral vascular disorder in a subject in need thereof, the peripheral vascular disorder being associated with excessive synthesis and secretion of a type IV collagen protein expressed by type IV collagen α5 or α6 genes, the method comprising administering a pharmaceutical composition comprising sirolimus as an active ingredient.

2. The method according to claim 1, wherein the peripheral vascular disorder has developed due to scleroderma.

3. The method according to claim 1, wherein the peripheral vascular disorder is a disorder associated with a condition selected from the group consisting of Raynaud's syndrome, pulmonary hypertension, interstitial lung disease, fibrosis of a digestive system, fibrosis of a kidney, fibrosis of a heart, and other vascular lesions associated with Raynaud's syndrome.

4. A method for inhibiting excessive synthesis and secretion of a type IV collagen protein expressed by type IV collagen α5 or α6 genes from a vascular endothelial cell, comprising applying sirolimus to the vascular endothelial cell.

5. The method according to claim 1, wherein the pharmaceutical composition comprising sirolimus is an oral preparation or a topical preparation.

6. The method according to claim 1, wherein the expression of type IV collagen is reduced in peripheral vascular cells of the subject after administering the pharmaceutical composition comprising sirolimus as the active ingredient.

* * * * *